(12) United States Patent
Lewallen (10) Patent No.: US 11,395,673 B2
(45) Date of Patent: Jul. 26, 2022

(54) FOLLICLE EXTRACTION SYSTEM AND RELATED METHODS (71) Applicant: Infuez, LLC, Woodinville, WA (US)

(72) Inventor: Scott Lewallen, Duvall, WA (US)

(*) Notice: Subject to any disclaimer, the term of this patent is extended or adjusted under 35 U.S.C. 154(b) by 317 days.

(21) Appl. No.: 16/572,481

(22) Filed: Sep. 16, 2019

(65) Prior Publication Data
US 2020/0008833 A1    Jan. 9, 2020

Related U.S. Application Data (62) Division of application No. 15/121,327, filed as application No. PCT/US2015/017665 on Feb. 26, 2015, now Pat. No. 10,448,968.

(60) Provisional application No. 61/944,749, filed on Feb. 26, 2014.

(51) Int. Cl.
*A61B 17/3205* (2006.01)
*A61B 17/00* (2006.01)
*A61B 17/32* (2006.01)

(52) U.S. Cl.
CPC .............. *A61B 17/32053* (2013.01); *A61B 2017/00752* (2013.01); *A61B 2017/320064* (2013.01)

(58) Field of Classification Search
CPC .......... A61B 2017/00743; A61B 2017/00747; A61B 2017/00752; A61B 2017/00969; A61B 2017/320064; A61B 2017/32007; A61B 2017/3225; A61B 17/32; A61B 17/32002; A61B 17/322; A61B 17/32053; A61B 17/34; A61B 17/54; A61B 17/545; A61B 2217/005; A61B 2217/007; A61B 2018/00315; A61B 2018/00452; A61B 2018/00476; A61B 10/02; A61B 10/0233;
(Continued)

(56) References Cited

U.S. PATENT DOCUMENTS

| 3,618,611 A | 11/1971 | Urban |
| 3,867,942 A | 2/1975 | Bellantoni et al. |
| 5,275,609 A | 1/1994 | Pingleton et al. |

(Continued)

FOREIGN PATENT DOCUMENTS

| KR | 10-0512694 | 5/2003 |
| KR | 10-2007-0037577 | 4/2007 |

(Continued)

*Primary Examiner* — Robert A Lynch
(74) *Attorney, Agent, or Firm* — Janeway Patent Law PLLC; John M. Janeway (57) ABSTRACT

A follicle container includes a receptacle to hold a hair follicle extracted from skin by a follicle extractor; a conduit, coupleable with the follicle extractor, to convey the extracted hair follicle toward the receptacle; and an injector to aerosolize and inject an irrigant into the conduit while the extracted hair follicle travels toward the receptacle. By injecting an irrigant into the conduit, the extracted follicle is less likely to be damaged on its journey to the receptacle. The irrigant lubricates the interior wall of the conduit and thus reduces friction between the extracted follicle and the wall as the follicle travels in the conduit. The irrigant also washes the interior of the conduit and keeps the extracted follicle moist and flexible. Flexibility allows the follicle to more easily suffer without damage bumps with the wall of the conduit and/or other extracted follicles as the follicle travels in the conduit.

17 Claims, 5 Drawing Sheets

(58) Field of Classification Search
CPC ...... A61B 2010/045; A61F 2/10; A61F 2/105;
B24C 3/065
See application file for complete search history.

(56) References Cited

U.S. PATENT DOCUMENTS

| | | |
|---|---|---|
| 5,611,811 A | 3/1997 | Goldberg |
| 5,782,843 A | 7/1998 | Aasberg |
| 5,827,297 A | 10/1998 | Boudjema |
| 5,895,403 A | 4/1999 | Collinsworth |
| 5,989,279 A | 11/1999 | Rassman |
| 6,027,512 A * | 2/2000 | Bridges ............... A61B 17/322 |
| | | 606/131 |
| 6,213,971 B1 | 4/2001 | Poole |
| 7,156,856 B2 | 1/2007 | Feller |
| 7,172,604 B2 | 2/2007 | Cole |
| 7,261,721 B2 | 8/2007 | Feller |
| 7,452,367 B2 | 11/2008 | Rassman et al. |
| 7,621,933 B2 | 11/2009 | Bodduluri et al. |
| RE42,381 E | 5/2011 | Gildenberg |
| RE42,437 E | 6/2011 | Gildenberg |
| RE42,438 E | 6/2011 | Gildenberg |
| 8,182,493 B2 | 5/2012 | Cole |
| 8,202,279 B2 | 6/2012 | Cole |
| 8,211,117 B2 | 7/2012 | Harris |
| 8,211,134 B2 | 7/2012 | Oostman, Jr. |
| 8,298,246 B2 | 10/2012 | Oostman, Jr. |
| 2003/0040766 A1 | 2/2003 | Werner |
| 2003/0097144 A1 | 5/2003 | Lee |
| 2003/0212415 A1 * | 11/2003 | Karasiuk ............... B24C 3/065 |
| | | 606/131 |
| 2005/0267506 A1 | 12/2005 | Harris |
| 2006/0161179 A1 | 7/2006 | Kachenmeister |
| 2006/0178678 A1 | 8/2006 | Cole |
| 2007/0038146 A1 * | 2/2007 | Quick ............... A61B 10/0275 |
| | | 600/566 |
| 2007/0156164 A1 | 7/2007 | Cole et al. |
| 2007/0255293 A1 | 11/2007 | Corre |
| 2007/0293884 A9 | 12/2007 | Cole et al. |
| 2008/0027384 A1 | 1/2008 | Wang et al. |
| 2008/0033455 A1 | 2/2008 | Rassman et al. |
| 2009/0088776 A1 | 4/2009 | Harris |
| 2010/0081989 A1 | 4/2010 | Berbers |
| 2010/0114118 A1 | 5/2010 | Harris |
| 2010/0125287 A1 | 5/2010 | Cole et al. |
| 2011/0060321 A1 | 3/2011 | Chandler et al. |
| 2012/0184969 A1 | 7/2012 | Melendez et al. |
| 2012/0215231 A1* | 8/2012 | Wesley ............ A61B 17/32053 |
| | | 606/133 |
| 2012/0265216 A1 | 10/2012 | Cole |
| 2012/0296344 A1 | 11/2012 | Cole |
| 2013/0023902 A1 | 1/2013 | Oostman, Jr. |
| 2014/0031839 A1 | 1/2014 | Umar et al. |

FOREIGN PATENT DOCUMENTS

| | | |
|---|---|---|
| WO | 2007041267 | 4/2007 |
| WO | 2007087463 | 8/2007 |
| WO | 2010057018 | 5/2010 |
| WO | 2014028626 | 2/2012 |

\* cited by examiner

FOLLICLE EXTRACTION SYSTEM AND RELATED METHODS

CROSS REFERENCE TO RELATED APPLICATION AND CLAIM OF PRIORITY

This application claims priority from commonly owned U.S. Provisional Patent Application 61/944,749 filed 26 Feb. 2014, and titled "Follicular Extraction System and Related Methods", incorporated by reference.

BACKGROUND

Transplanting a hair from one region of a person's body to another region of the body is frequently done to add hair to the other region that may not have any hair or may have a small amount of hair. To make the transplanted hair and its new location look as natural as possible, the hair that is transplanted should be viable when it is sown at the new location. To do this successfully one must extract the hair's follicle from its position in the skin and then transport the follicle to the transplant location.

Because a hair's follicle is small, a typical transplant procedure includes transplanting many individual hairs. And because a hair's follicle is fragile, one must take care during the transplant procedure to not damage the follicle. A common way to protect and keep an extracted follicle viable is to keep the follicle bathed in saline solution until the follicle is sown at the new location. Thus, one could transplant many hairs to a new location by extracting, transporting and then sowing, individually, each hair before extracting the next hair. This process could increase the viability of each hair by reducing the amount of time that each follicle spends separated from skin, but the time that it would take to perform such a procedure would be very long; more than most people have to spend on such a procedure.

To reduce the time spent transplanting many hairs to a new location, many procedures involve extracting all or many hairs before sowing the hairs at the new location. To help keep the extracted hairs viable until they are sown, the hairs are typically transported from the extraction tool to a receptacle containing saline solution, via a tube. Then, when one is ready to sow the hair at the new location, one separates the hair follicles from the saline solution and sows them. Unfortunately, many hair follicles are damaged as they travel through the tube into the receptacle. And, such damage often reduces the viability of the hair follicle at the new location.

SUMMARY

In an aspect of the invention, a follicle container for transporting an extracted hair follicle from a follicle extractor and containing the hair follicle for future use includes a receptacle to hold a hair follicle extracted from skin by a follicle extractor; a conduit, coupleable with the follicle extractor, to convey the extracted hair follicle toward the receptacle; and an injector to aerosolize and inject an irrigant into the conduit while the extracted hair follicle travels toward the receptacle.

By injecting an irrigant into the conduit, the extracted follicle is less likely to be damaged on its journey to the receptacle. The irrigant lubricates the interior wall of the conduit and thus reduces friction between the extracted follicle and the wall as the follicle travels in the conduit. The irrigant also washes the interior of the conduit and keeps the extracted follicle moist and thus viable and more flexible as the follicle travels in the conduit. Flexibility allows the follicle to more easily suffer without damage bumps with the wall of the conduit and/or other extracted follicles as the follicle travels in the conduit.

In another aspect of the invention, a system for extracting and containing a hair follicle from skin includes a follicle extractor to extract a hair follicle from skin; and a follicle container coupled with the follicle extractor, to transport a hair follicle extracted by the follicle extractor, and hold the hair follicle for future use. The follicle container includes a receptacle to hold the extracted hair follicle, a conduit to convey the extracted hair follicle toward the receptacle, and an injector to aerosolize and inject an irrigant into the conduit while the extracted hair follicle travels toward the receptacle.

DETAILED DESCRIPTION

Figure 1:
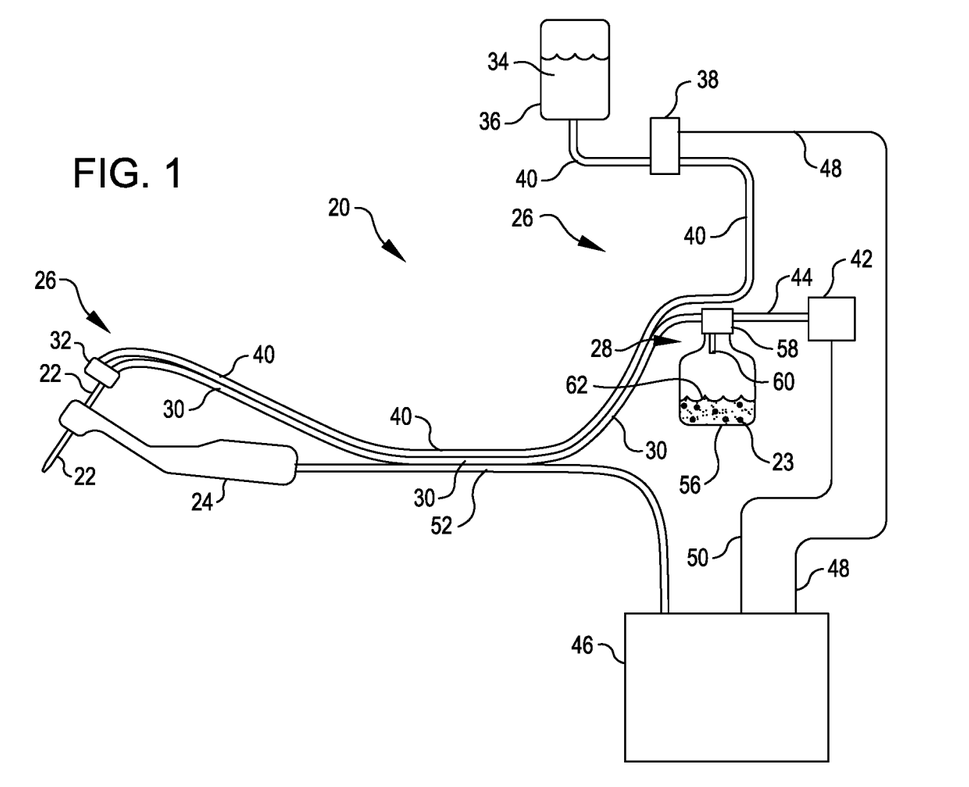
FIG. 1 shows a system for extracting and containing a hair follicle from skin, according to an embodiment of the invention.
Figure 2:
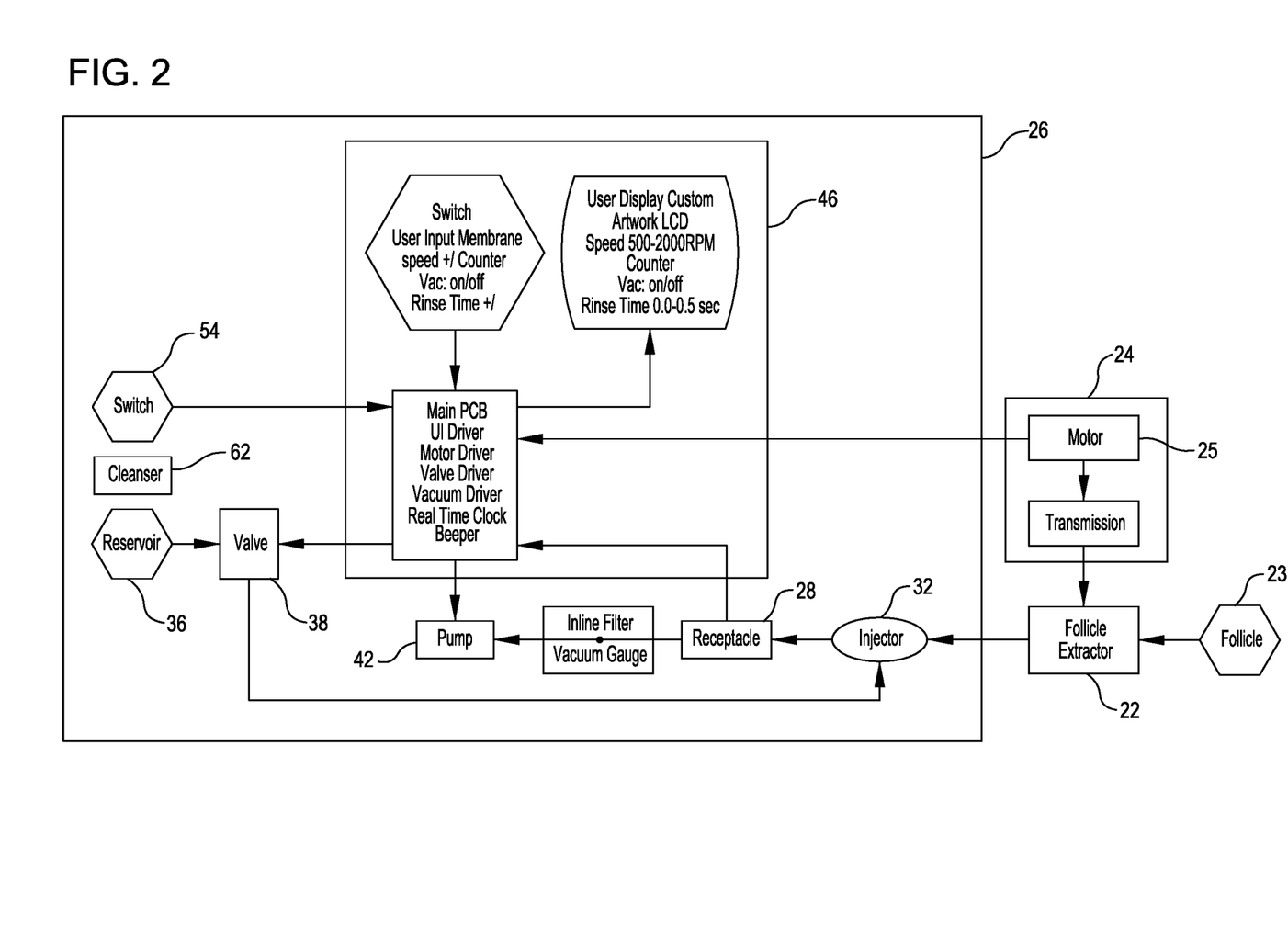
FIG. 2 shows a block diagram of the system shown in FIG. 1, according to an embodiment of the invention.

FIG. 1 shows a system 20 for extracting and containing a hair follicle from skin, according to an embodiment of the invention. FIG. 2 shows a block diagram of the system 20, also according to an embodiment of the invention. The system 20 includes a follicle extractor 22 (discussed in greater detail in conjunction with FIGS. 3 and 4) to extract a follicle 23 from a person's scalp or skin (not shown), and a handpiece 24 that includes a motor 25 (in FIG. 2) to power the follicle extractor 22. The system 20 also includes a follicle container 26 to transport the extracted hair follicle from the extractor 22, and to contain the hair follicle for future use, such as as a transplant to a different location. The follicle container 26 includes a receptacle 28 to hold the extracted hair follicle, a conduit 30 to convey the extracted hair follicle toward the receptacle 28, and an injector 32 (discussed in greater detail in conjunction with FIGS. 5-7) to aerosolize and inject an irrigant 34 into the conduit 30 while the extracted hair follicle travels toward the receptacle 28.

By injecting an irrigant 34 into the conduit 30, the extracted follicle is less likely to be damaged on its journey to the receptacle 28. The irrigant 34 lubricates the interior wall (not shown) of the conduit 30 and thus reduces friction between the extracted follicle and the wall as the follicle travels in the conduit 30. The irrigant 34 also washes the interior of the conduit 30 and keeps the extracted follicle moist and thus viable and more flexible as the follicle travels in the conduit 30. Flexibility allows the follicle to more easily suffer, without damage, bumps with the wall of the conduit 30 and/or other extracted follicles as the follicle travels in the conduit 30.

Although the system 20 shown in FIG. 1 includes a follicle extractor 22 and a handpiece 24, both the extractor 22 and the handpiece 24 may be omitted from the system 20. In such embodiments, the follicle container 26 may be coupled to any desired follicle extractor to transport and contain a hair follicle extracted by the coupled extractor.

The follicle container 26 also includes a reservoir 36 that holds irrigant 34, a valve 38 that controls the flow of irrigant 34 from the reservoir 36 toward the injector 32, and a tube 40 that couples the reservoir 36 to the injector 32 to carry the irrigant 34 from the reservoir 36 to the injector 32. In addition, the follicle container 26 includes a pump 42 coupled to the receptacle 28 via a tube 44, and a controller 46 to control the valve 38, and the pump 42 via one of the respective cables 48 and 50. In the embodiment of the system 20 shown in FIGS. 1 and 2, the controller 46 also controls the motor 25 of the handpiece 24 via the cable 52.

In this and other embodiments, the pump 42 pulls air out of the receptacle 28 and conduit 30 to reduce the pressure inside the receptacle 28 and conduit 30 below atmospheric pressure. Because the follicle extractor 22 and injector 32 are coupled to the conduit 30, the pump 42 also reduces the pressure inside the follicle extractor 22, the injector 32, the tube 40 and the reservoir 36, below atmospheric pressure. This reduction in pressure throughout the follicle container 26 provides two functions. The reduction in pressure in the follicle extractor 22 and conduit 30 causes a hair follicle that the extractor 22 has prepared for extraction to move through the injector 32 toward the receptacle 28. And, the reduction in pressure in the injector 32, tube 40 and the reservoir 36 causes irrigant 34 to move from the reservoir 36 to the injector 32 and then enter the conduit 30. When the valve 38 is open irrigant flows out of the reservoir 36 toward the injector 32; when the valve 38 is closed irrigant does not flow out of the reservoir 36. To prepare a hair follicle for extraction from a person's scalp or skin, a medical practitioner positions the follicle extractor 22 over the follicle such that the extractor 22 contacts the person's skin. The medical practitioner then operates a switch 54 (shown in FIG. 2) that causes the motor to rotate the extractor 22 to cut the tissue around the hair follicle that the extractor 22 contacts.

The pressure inside the follicle container 26 may be any desired pressure and the pump 42 may be any desired pump capable of generating the desired pressure. For example, in this and other embodiments the pressure generated inside the follicle container 26 is about 20 inches of mercury (about 9.82 pounds per square inch) below atmospheric pressure. And the pump 42 is a conventional pump that pulls or sucks air out of the receptacle 28 to reduce the pressure inside the follicle container 26 below atmospheric pressure. In other embodiments the pressure generated inside the follicle container 26 may be more than 20 inches of mercury below atmospheric pressure, such as 30 inches of mercury (about 14.73 pounds per square inch), or less than 20 inches of mercury below atmospheric pressure, such as 15 inches of mercury (about 7.36 pounds per square inch). In addition, in other embodiments the pump 42 may be a conventional pump that pushes or injects air into the follicle container 26 to generate pressure inside the container 26 that is greater than atmospheric pressure. In such embodiments, the pump 42 could be located closer to the follicle extractor 22, and the pump 42 could have an outlet located at the tip of the extractor 22 so that an extracted follicle would be urged to travel toward the receptacle 28.

Still referring to FIGS. 1 and 2, the receptacle 28 may be configured as desired to capture and hold an extracted hair follicle 23 for future use. For example, in this and other embodiments, the receptacle 28 includes a bottle 56 (in FIG. 1) that holds the extracted follicles 23, and a top 58 that effectively separates the conduit 30 that couples the injector 32 to the receptacle 28, from the tube 44 that couples the receptacle 28 to the pump 42. By separating the conduit 30 from the tube 44, one can isolate an extracted follicle 23 from the air that carries it from the follicle extractor 22 to the bottle 56. When the extracted follicle 23 exits the end 60 of the conduit 30, the follicle 23 drops into the saline solution 62 disposed at the bottom of bottle 56 while the air that carried the follicle flows away from the saline solution toward the top 58 and into the tube 44 toward the pump 42. To keep large particulates from leaving the bottle 56, a strainer (not shown) is positioned in the top 58 covering the opening of the tube 44. And to keep aerosolized fluids from reaching the pump 44, a filter that includes a hydrophobic membrane, such as Polytetrafluoroethylene (PTFE), is positioned in the tube 44. The receptacle 28 also includes a sensor, such as a conventional optical sensor, to warn when the bottle 56 is full or is close to getting full.

Still referring to FIGS. 1 and 2, the reservoir 36 and valve 38 may be any desired reservoir and valve that are capable of delivering irrigant 34 to the injector 32 when needed. For example, in this and other embodiments the reservoir 32 is flexible to allow the ambient air pressure to push the irrigant out of the reservoir 36 and into the tube 40, and the valve 38 is a conventional pinch-valve that stops the flow of irrigant toward the injector 32 by pinching or clamping the tube 40 shut, and allows the irrigant to flow toward the injector 32 by partially pinching or clamping the tube 40 shut. In other embodiments the reservoir 36 may be rigid and vented to ambient air to allow irrigant 34 to flow toward the injector 32 when the valve 38 is open. In still other embodiments, the reservoir 36 may include a pump to move the irrigant 34 toward the injector 32.

Still referring to FIGS. 1 and 2, the irrigant 34 may be any desired irrigant capable of lubricating an extracted follicle's travel through the conduit 30 and preserving the viability of the extracted follicle 23 for future use as a transplant. For example, in this and other embodiments, the irrigant 34 includes normal saline solution or 0.9% sodium chloride (about 9.0 grams of sodium chloride dissolved in one liter of water). In other embodiments, the irrigant 34 may include Lactated Ringer's solution.

Still referring to FIGS. 1 and 2, the controller 46 may be configured as desired to control the operation of the system 20. For example, in this and other embodiments the controller 46 controls the motor 25 in the handpiece 24, the pinch valve 38, and the pump 42. The controller 46 may control these within two, separate control modes—short-hair mode and long-hair mode. In either mode, the medical practitioner starts and stops the motor 25, and thus the rotation of follicle extractor 22, by working the switch 54 (here a pedal that the practitioner works with his/her foot). After extracting a hair follicle the practitioner stops the motor 25 to position the follicle extractor 22 over the next hair follicle to be extracted. When the practitioner starts the motor 25 to extract the first hair follicle of the procedure, the controller 46 starts the pump 42. The pump 42 remains on while the motor 25 powers the follicle extractor 22. Then, when the practitioner stops the motor 25, the controller keeps the pump 42 on and opens the pinch-valve 38 for a period (here about 0.15 seconds) to allow irrigant 34 to flow toward the injector 32. If the practitioner has set the controller 46 to operate in short-hair mode, then the pump 42 remains on for the whole period that the motor 25 is stopped between successive hair follicle extractions. If the practitioner has set the controller 46 to operate in long-hair mode, then the pump 42 remains on for a period (here about 2.0 seconds), then turns off to allow the practitioner to position the follicle extractor 22 over the next long hair and its follicle without the air flowing through the follicle extractor 22 making the long hair uncontrollable.

Other embodiments are possible. For example, the controller 46 may include a single operating mode or more than two operating modes. In addition, the pinch-valve 38 may be opened at other moments during the extraction procedure, such as while the follicle extractor 22 is rotating. Also, the pinch-valve 38 may be opened for a period that is shorter than or longer than 0.15 seconds, and may be pulsed, or repeatedly opened and closed, while a hair follicle is being extracted. In addition, in the long-hair mode the period that the pump 42 remains on after the motor 25 has stopped may be shorter than or longer than 2.0 seconds. Also, in the short-hair mode the pump 42 may be turned off for a period before the follicle extractor 22 is powered for the next hair follicle extraction.

Still referring to FIGS. 1 and 2, the system 20 may also include a cleanser 62 (discussed in greater detail in conjunction with FIGS. 8 and 9) to clear the follicle extraction tool 22 during an extraction procedure.

Figure 3:
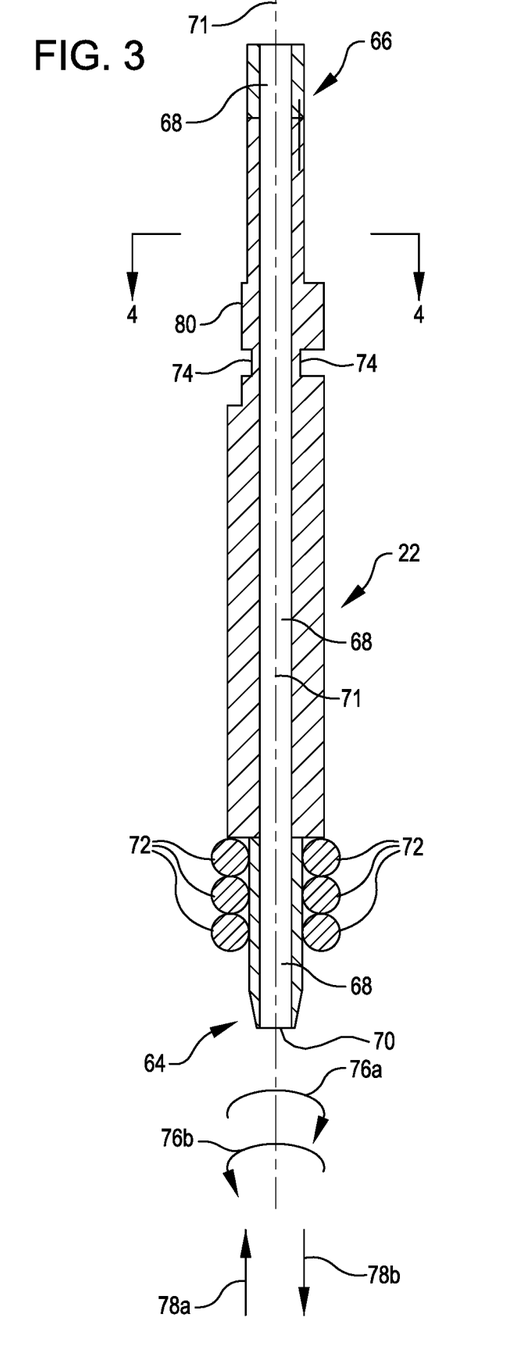
FIG. 3 shows a cross-sectional view of a follicle extractor shown in FIGS. 1 and 2, according to an embodiment of the invention.
Figure 4:
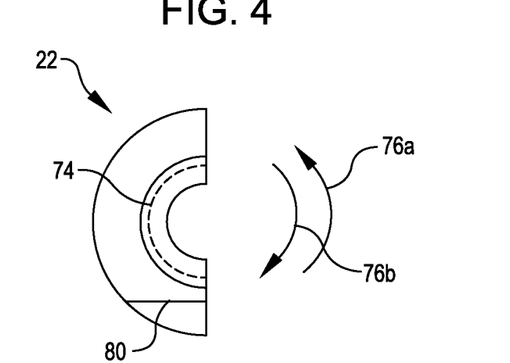
FIG. 4 shows a different cross-sectional view of the follicle extractor shown in FIG. 3, according to an embodiment of the invention.

FIG. 3 shows a cross-sectional view of a follicle extractor 22 shown in FIGS. 1 and 2, according to an embodiment of the invention. FIG. 4 shows a different cross-sectional view of the follicle extractor 22 shown in FIG. 3, also according to an embodiment of the invention. The follicle extractor 22 helps the follicle container 26 (FIGS. 1 and 2) extract a follicle 23 (FIGS. 1 and 2) from a person's scalp or skin (not shown) by cutting tissue around the hair follicle that anchors the follicle in the skin.

The follicle extractor 22 may be configured as desired to biopsy a live hair follicle. For example, in this and other embodiments the extractor 22 includes a first end 64, a second end 66 and a bore 68 that extends from the first end 64 to the second end 66. The first end 64 includes a cutting edge 70 that slices tissue when the extractor 22 is rotated by the motor 25 (FIG. 2). The second end 66 couples the injector 32 (FIGS. 1, 2 and 5-7) to the follicle extractor 22. The bore 68 is sized to allow a hair follicle to travel through it unrestricted from the first end 64 to the second end 66. The bore 68 is also continuous—that is, sealed within the extractor 22 except for at the first and second ends 64 and 66, respectively. This protects the hair follicle as it travels through the handpiece 24 by preventing contact with the ambient environment. This continuous bore 68 also allows one to easily clean the extractor 22 and the handpiece 24 after a procedure.

To extract a hair follicle, the medical practitioner positions the follicle extractor 22 over the follicle such that the hair extending from the follicle lies in the bore 68, and the cutting edge 70 contacts the skin above the follicle. The motor 25 then rotates the follicle extractor 22 about the extractor's longitudinal axis 71 so that the cutting edge 70 slices tissue around the follicle. This causes the hair follicle to enter the bore 68 in preparation for traveling in the conduit 30 (FIG. 1) toward the receptacle 28 (FIG. 1). To prevent the medical practitioner from cutting to deep into the patient's scalp or skin, the follicle extractor 22 includes a stop 72 (here three) that the practitioner can place onto or remove from the first end 64. When the stop 72 contacts the patient's skin, the stop 72 makes further insertion of the first end 64 into the patient's scalp or skin difficult, and thus signals to the practitioner that the desired depth has been reached.

Still referring to FIGS. 3 and 4, in this and other embodiments the follicle extractor 22 includes a groove 74 that receives a collar (not shown) in the handpiece 24 to retain the extractor 22 to the handpiece 24 while the motor 25 rotates the extractor 22. When the collar is inserted into the groove 74 the collar allows the extractor 22 to rotate in the directions shown by arrows 76a and 76b, while preventing substantial movement of the extractor 22 in the direction of the arrows 78a and 78b. The extractor 22 also includes a flat 80 that the transmission (not shown) of the handpiece 24 engages so that the motor 25 can rotate the extractor 22.

Other embodiments are possible. For example, the follicle extractor 22 may be configured to extract a hair follicle by reciprocating a cutting edge, not spinning a cutting edge. In such embodiments, the follicle extractor 22 may be very similar to the follicle extractor 22 shown in FIGS. 3 and 4, but the motor 25 or the transmission that couples the motor 25 to the extractor 22 may cause the extractor 22 to rotate about the longitudinal axis 71 for a desired angular distance and then reverse the rotation for another desired angular distance.

Figure 5:
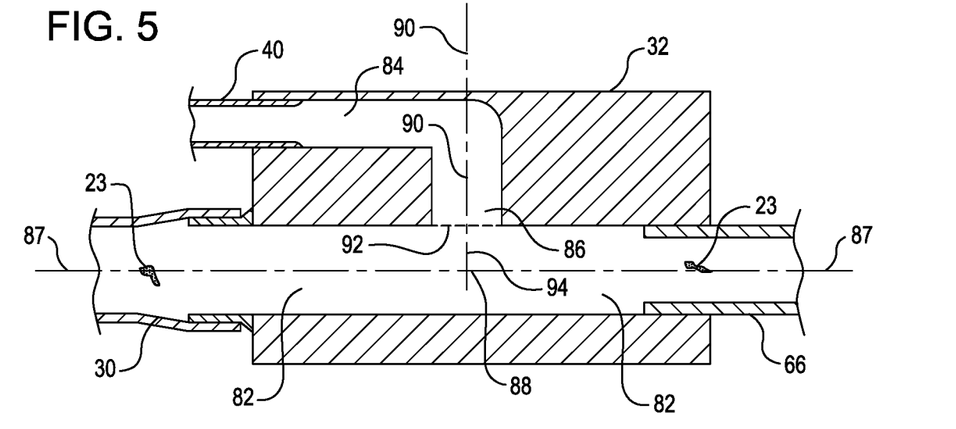
FIG. 5 shows a cross-sectional view of an injector shown in FIGS. 1 and 2, according to an embodiment of the invention.
Figure 6:
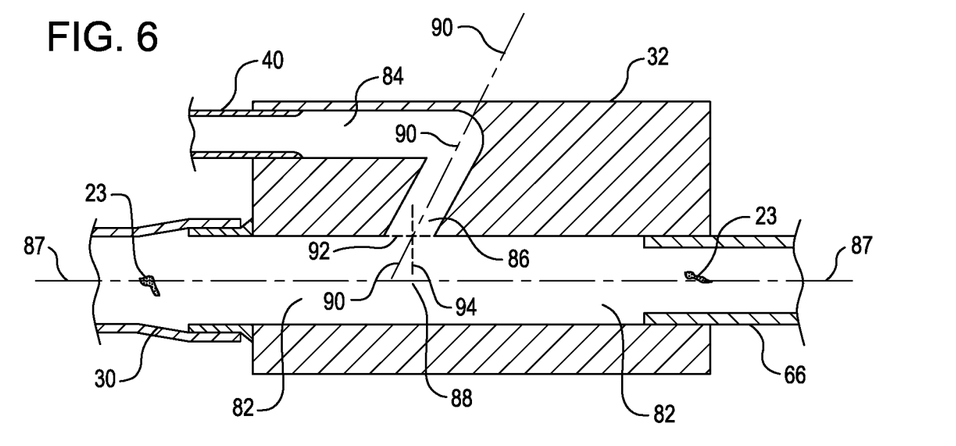
FIG. 6 shows a cross-sectional view of an injector shown in FIGS. 1 and 2, according to another embodiment of the invention.
Figure 7:
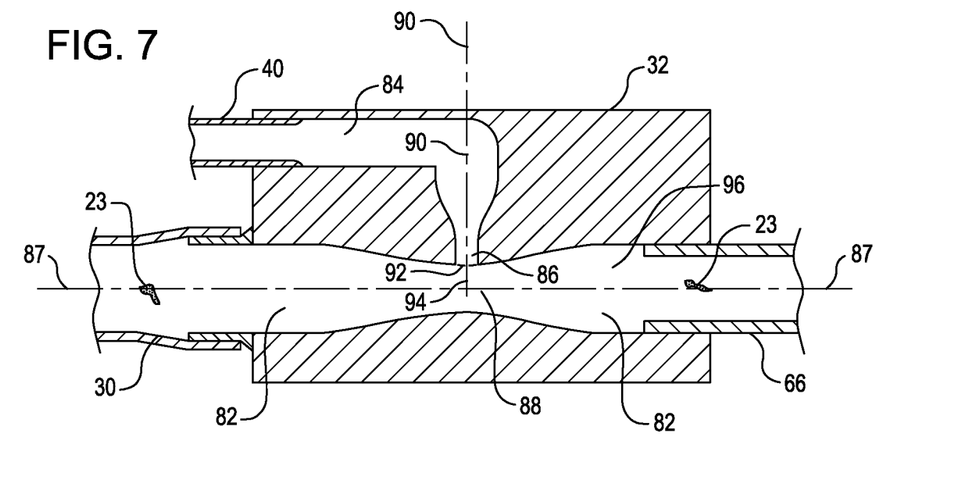
FIG. 7 shows a cross-sectional view of an injector shown in FIGS. 1 and 2, according to yet another embodiment of the invention.

Each of FIGS. 5, 6 and 7 shows a cross-sectional view of an injector 32 shown in FIGS. 1 and 2 according to an embodiment of the invention. The injector 32 aerosolizes and injects an irrigant 34 (FIG. 1) into the conduit 30 while an extracted hair follicle 23 travels toward the receptacle 28. In aerosolized form, the irrigant 34 is more easily and readily dispersed throughout the conduit 30 as an extracted follicle 23 travels through the injector 32, and thus more thoroughly covers the whole of the extracted follicle 23. In aerosolized form the irrigant 34 is also more likely to remain on the extracted follicle 23 as the follicle 23 travels in the conduit 30 toward the receptacle 28. In addition, when the irrigant 34 is aerosolized, the irrigant cools the conduit 30, and the follicle container 26 consumes less irrigant 34 than if the irrigant was not aerosolized.

In this and other embodiments, the injector 32 includes a first passage 82 and a second passage 84 that has a port 86 through which irrigant 34 flows to enter the first passage 82. The first passage 82 is coupled to the conduit 30 and the second end 66 of the follicle extractor 22 such that the extracted follicle 23 travels through the injector's first passage 82 on its way to the receptacle 28. While the follicle extractor 22 rotates the injector 32 does not. To accomplish this the inside diameter of the portion of the first passage 82 that contacts the second end 66 of the extractor 22 is a little longer than the outside diameter of the extractor's second end 66. This difference in the lengths reduces the force generated by friction between the injector 32 and the extractor's second end 66 that resists their movement relative to each other. To help further reduce the force generated by friction, the injector 32 may include at the inside diameter of the first passage 82 a material that has a low coefficient of friction when contacting the material of the extractor's second end 66. In addition, a lubricant may be disposed between the material of the first passage and the extractor's second end 66. The second passage 84 is coupled to the tube

40 (FIG. 1) that carries irrigant 34 from the reservoir 36 (FIG. 1) to the injector 32. When the pump 42 generates a vacuum in the conduit 30, the vacuum reaches into the second passage 84 and tube 40 through the port 86, and urges irrigant 34 to flow through the second passage 84 and port 86 into the first passage 82.

Still referring to FIGS. 3, 4 and 5, the port 86 may be configured as desired to aerosolize the irrigant 34 as the irrigant 34 enters the first passage 82. For example, in this and other embodiments, the first passage 82 includes a longitudinal axis 87 and a throat 88 where the port 86 is located, and the port 86 includes a longitudinal axis 90, a cross-sectional area 92 and a port axis 94. The port's longitudinal axis 90 indicates the general direction that the irrigant travels as it enters the throat 88. The cross-sectional area 92 is the area of the port 86 at the intersection of the port 86 with the throat 88. And the port axis 94 is perpendicular to the cross-sectional area 92 and indicates the orientation of the cross-sectional area 92 relative to the throat 88.

In the embodiment shown in FIG. 5, the port 86 is configured such that the port's longitudinal axis 90 is substantially perpendicular to the first passage's longitudinal axis 87, and the cross-sectional area of the port 86 is substantially constant and equal to the cross-sectional area 92. Thus, the port's axis 94 is aligned or parallel to the port's longitudinal axis 90. In this configuration the irrigant 34 is injected into the throat 88 at about 90 degrees relative to the flow of air through the throat 88. At this angle, the air flowing through the throat 88 violently collides with the irrigant 34 causing the air to shear the droplets of irrigant 34 into smaller droplets. This shearing combined with the low air pressure in the throat 88 causes the droplets of irrigant 34 to aerosolize into a mist when they enter the throat 88.

In the embodiment shown in FIG. 6, the port 86 is configured such that the port's longitudinal axis 90 is oriented relative to the first passage's longitudinal axis 87 at an angle other than 90 degrees, and the cross-sectional area of the port 86 is substantially constant and less than the cross-sectional area 92. Thus, the port's axis 94 lies at angle less than 90 degrees relative to the port's longitudinal axis 90. In this configuration the irrigant 34 is injected into the throat 88 in a direction similar to the flow of air through the throat 88. At such angles, the air flowing through the throat 88 collides less violently with the irrigant 34 reducing the shearing effect on the droplets of irrigant 34 into smaller droplets. Thus, the irrigant 34 may be aerosolized into a mist having larger droplets than the mist generated with the injector 32 shown in FIG. 5.

In the embodiment shown in FIG. 7, the port 86 is configured such that the port's longitudinal axis 90 is substantially perpendicular to the first passage's longitudinal axis 87, and the cross-sectional area of the port 86 gets smaller as the irrigant 34 flows toward the throat 88. In addition, the throat 88 includes an entrance 96 having a cross-sectional area, an exit 98 having a cross-sectional area, and an intermediate region where the port 86 is located. The intermediate region also has a cross-sectional area, which is less than the entrance's cross-sectional area and less than the exit's cross-sectional area, yet large enough to allow an extracted hair follicle 23 to travel through the intermediate region without getting stuck. By reducing the cross-sectional area of the port 86 along the port axis 90, one can increase the speed at which the irrigant 34 enters the throat 88. Similarly, by reducing the cross-sectional area of the throat 88 where the port 86 is located, one can increase the speed at which the air flows across the port 86. In such configurations the air flowing through the throat 88 collides more violently with the irrigant 34 than in the injector 32 shown in FIG. 5, causing the air to shear the droplets of irrigant 34 into smaller droplets. Thus, the irrigant 34 may be aerosolized into a mist having smaller droplets than the mist generated with the injector 32 shown in FIG. 5.

Other embodiments of the injector 32 are possible. For example, the injector 32 may be configured to inject irrigant 34 into the throat 88 but not aerosolize the irrigant 34. In such embodiments, the port 86 may be configured such that the port's longitudinal axis 90 and the port axis 94 are aligned or parallel with each other, and oriented at an angle that is much less than 90 degrees, for example 20 degrees. In such embodiments, the irrigant 34 would still be capable of keeping an extracted follicle 23 moist while the follicle 23 travels toward the receptacle 28, and washing/splashing the conduit 30 to help prevent an extracted follicle from getting stuck in the conduit 30.

Figure 8:
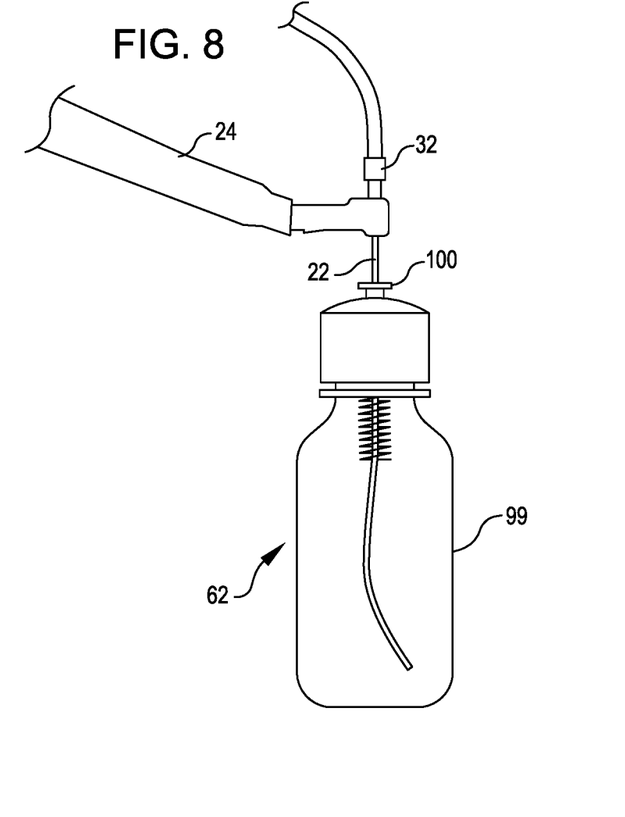
FIG. 8 shows a view of a cleanser for cleaning a follicle extractor that may be included in the system shown in FIGS. 1 and 2, according to an embodiment of the invention.
Figure 9:
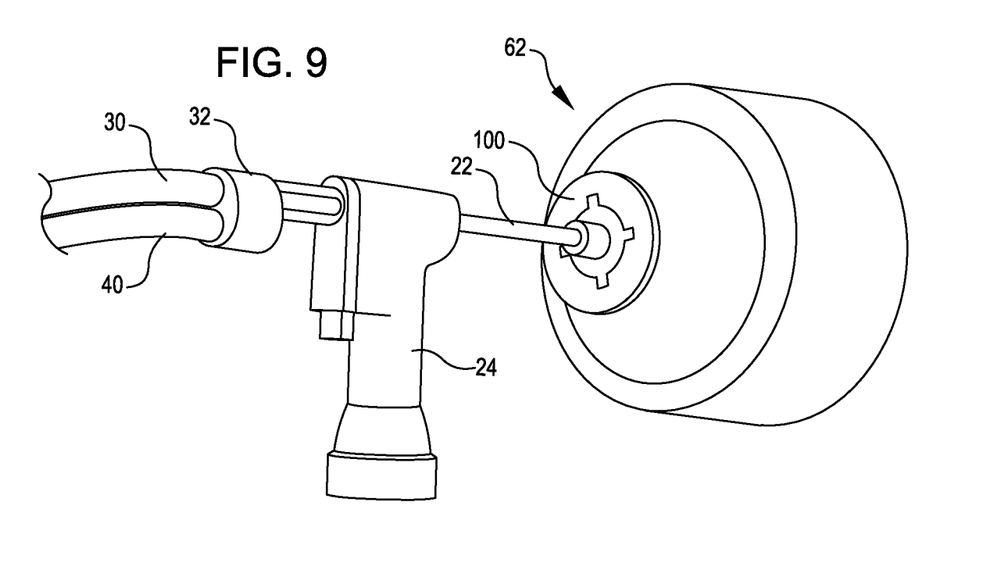
FIG. 9 shows another view of the cleanser shown in FIG. 8, according to an embodiment of the invention.

FIG. 8 shows a view of a cleanser 62 for cleaning a follicle extractor 22 that may be included in the system shown in FIGS. 1 and 2, according to an embodiment of the invention. FIG. 9 shows another view of the cleanser 62 shown in FIG. 8, according to an embodiment of the invention. A medical practitioner may use the cleanser 62 to clear a follicle extractor 22 that has become clogged during an extraction procedure, or to clean a follicle extractor 22 after completing a procedure.

The cleanser 62 may be configured as desired to clean a follicle extractor 22. For example, in this and other embodiments the cleanser 62 is similar to a conventional lotion dispenser in which one presses down on the dispenser to generate pressure inside the lotion dispenser's container, which then urges lotion out of the dispenser. Here, the cleanser 62 includes a jar 99 and a dispenser 100 that is configured to receive the extractor 22 (FIG. 3) and inject a dose (here a cc or so) of cleaner (here a saline solution) into the bore 68 (FIG. 3) of the extractor 22 when the dispenser 100 is moved toward the jar 99. In other embodiments, insertion of the extractor's first end 64 (FIG. 3) into the dispenser 100, or contact of the stop 72 (FIG. 3) with the dispenser 100 may trigger the cleanser 62 to inject a dose of cleaner into the bore 68. In still other embodiments, the stop 72 may simply position the extractor 22 in the dispenser 100, after which, the practitioner may squeeze the jar 99 or otherwise generate pressure inside the jar 99 to inject a dose of cleaner into the bore 68.

The preceding discussion is presented to enable a person skilled in the art to make and use the invention. Various modifications to the embodiments will be readily apparent to those skilled in the art, and the generic principles herein may be applied to other embodiments and applications without departing from the spirit and scope of the present invention. Thus, the present invention is not intended to be limited to the embodiments shown, but is to be accorded the widest scope consistent with the principles and features disclosed herein.

What is claimed is:

1. A system for transporting an extracted hair follicle from a follicle extractor and containing the hair follicle for future use, the system comprising:
   a receptacle operable to hold a hair follicle extracted from skin by a follicle extractor;
   a conduit, coupleable with the follicle extractor, and operable to convey the extracted hair follicle toward the receptacle; and
   an injector operable to aerosolize and inject an irrigant into the conduit at a location between the receptacle and an entrance of the conduit, while the extracted hair follicle travels through the conduit toward the receptacle.

2. The system of claim 1 wherein the receptacle is coupled with a pump operable to move air through the conduit and receptacle to urge the extracted hair follicle to travel toward the receptacle.

3. The system of claim 1 wherein:
the receptacle is coupled with a pump operable to move air through the conduit and receptacle to urge the extracted hair follicle to travel toward the receptacle, and
the receptacle is configured to trap the extracted hair follicle when the follicle enters the receptacle by allowing gravity to move the follicle out of the air moving through the receptacle.

4. The system of claim 1 wherein the receptacle is coupled with a pump operable to reduce pressure in the conduit and the receptacle to urge the extracted hair follicle to travel toward the receptacle.

5. The system of claim 1 wherein the injector includes:
a first passage having a throat,
a second passage having a port disposed in the throat, and
wherein as the extracted hair follicle travels toward the receptacle:
the follicle travels through the throat of the first passage, and
the irrigant enters the first passage through the port in the throat.

6. The system of claim 5 wherein the irrigant is aerosolized as the irrigant enters the throat of the first passage.

7. The system of claim 5 wherein:
the throat of the first passage includes a longitudinal axis,
the port of the second passage includes a cross-sectional area located at the throat, and a port axis that is perpendicular to the cross-sectional area, and
the port is positioned in the throat such that the port axis is substantially perpendicular to the throat's longitudinal axis.

8. The system of claim 5 wherein:
the throat of the first passage includes a longitudinal axis, and
the port of the second passage includes a longitudinal axis and the port is positioned in the throat such that the port's longitudinal axis is substantially perpendicular to the throat's longitudinal axis.

9. The system of claim 5 wherein:
the throat includes an entrance having a first cross-sectional area, an exit having a second cross-sectional area, and an intermediate region between the entrance and the exit having a third cross-sectional area, that is less than each of the first and second cross-sectional areas, and
the port is positioned in the intermediate region.

10. The system of claim 5 wherein the port includes an entrance having a cross-sectional area and an exit disposed in the throat and having a cross-sectional area that is less than the cross-sectional area of the port's entrance.

11. A system for extracting and containing a hair follicle from skin, the system comprising:
a follicle extractor operable to extract a hair follicle from skin; and
a follicle container coupled with the follicle extractor, and operable to transport a hair follicle extracted by the follicle extractor, and hold the hair follicle for future use, wherein the follicle container includes:
a receptacle operable to hold the extracted hair follicle,
a conduit operable to convey the extracted hair follicle toward the receptacle, and
an injector operable to aerosolize and inject an irrigant into the conduit at a location between the receptacle and an entrance of the conduit, while the extracted hair follicle travels through the conduit toward the receptacle.

12. The system of claim 11 wherein the follicle extractor includes:
a first end having an edge operable to cut skin when the edge is moved across the skin,
a second end coupled with the injector, and
a bore extending from the first end to the second end and through which the hair follicle travels to reach the conduit of the follicle container.

13. The system of claim 11 wherein the follicle extractor rotates about a longitudinal axis to extract the hair follicle.

14. The system of claim 11 wherein:
the injector includes:
a first passage having a throat through which the extracted hair follicle travels as the follicle travels toward the receptacle,
a second passage having a port disposed in the throat and through which the irrigant enters the throat, and
the follicle container includes a reservoir of irrigant coupled with the injector, and operable to release irrigant to flow toward the injector when the extracted hair follicle travels through the injector's throat.

15. The system of claim 11 wherein the follicle container includes:
a reservoir of irrigant coupled with the injector, and
a valve operable to control the flow of irrigant toward the injector.

16. The system of claim 11 wherein the follicle container includes a reservoir to hold irrigant, and the reservoir includes a wall that is flexible so that ambient air pressure can urge the irrigant out of the reservoir and toward the injector.

17. A system for extracting and containing a hair follicle from skin, the system comprising:
a follicle extractor operable to extract a hair follicle from skin; and
a follicle container coupled with the follicle extractor, and operable to transport a hair follicle extracted by the follicle extractor, and hold the hair follicle for future use, wherein the follicle container includes:
a receptacle operable to hold the extracted hair follicle,
a conduit operable to convey the extracted hair follicle toward the receptacle,
an injector operable to aerosolize and inject an irrigant into the conduit while the extracted hair follicle travels toward the receptacle, and
a reservoir to hold irrigant, wherein the reservoir includes a wall that is flexible so that ambient air pressure can urge the irrigant out of the reservoir and toward the injector.

* * * * *